United States Patent [19]

Abramowitz et al.

[11] Patent Number: 5,536,507
[45] Date of Patent: Jul. 16, 1996

[54] COLONIC DRUG DELIVERY SYSTEM

[75] Inventors: Robert Abramowitz, Cranbury; Sunanda A. Ranadive, East Brunswick; Sailesh A. Varia, Plainsboro; Nemichand B. Jain, Cranbury, all of N.J.

[73] Assignee: Bristol-Myers Squibb Company, Princeton, N.J.

[21] Appl. No.: 265,167

[22] Filed: Jun. 24, 1994

[51] Int. Cl.⁶ .............................. A61K 9/32; A61K 9/36; A61K 9/58; A61K 9/62
[52] U.S. Cl. .................... 424/479; 424/480; 424/482; 424/493; 424/494; 424/495; 424/497
[58] Field of Search ....................... 424/474, 475, 424/479, 480, 482, 493, 494, 495, 497

[56] References Cited

U.S. PATENT DOCUMENTS

| | | | |
|---|---|---|---|
| 4,309,404 | 1/1982 | DeNeale et al. | 424/21 |
| 4,432,966 | 2/1984 | Zeitoun et al. | 413/21 |
| 4,837,030 | 6/1989 | Valarose, Jr. et al. | 424/456 |
| 4,882,169 | 11/1989 | Ventouras | 424/493 |
| 4,910,021 | 3/1990 | Davis et al. | 424/463 |
| 5,283,065 | 2/1994 | Doyon et al. | 424/467 |
| 5,326,570 | 7/1994 | Rudnic et al. | 424/458 |

FOREIGN PATENT DOCUMENTS

0312340A1  4/1989  European Pat. Off. .

OTHER PUBLICATIONS

S.S. Davis, "The Design and Evaluation of Controlled Release Systems for the Gastrointestinal Tract", *J. of Controlled Release*, 2, (1985) 27–38.

Remington's Pharmaceutical Sciences, 1990, 18th. Edition, Philadelphia College of Pharmacy and Science, Chapter 66, Pharmaceutical Necessities, pp. 1305, 1313, & 1327.

*Primary Examiner*—Thurman K. Page
*Assistant Examiner*—James M. Spear
*Attorney, Agent, or Firm*—Ellen K. Park

[57] ABSTRACT

A three component pharmaceutical formulation of one or more pharmacologically active substances such that greater than 80% of the pharmacologically active substance will be released in the large intestine. The first component comprises the pharmacologically active substance, microcrystalline cellulose, a pH-sensitive polymer, and optionally an osmotic agent. The second component is a delayed release coating, and the third component is an enteric coating.

15 Claims, No Drawings

COLONIC DRUG DELIVERY SYSTEM

BRIEF DESCRIPTION OF THE INVENTION

The present invention is directed to a pellet formulation of a pharmacologically active substance such that greater than 80% of the pharmacologically active substance is released in the regions of the large intestine. The controlled release delivery of the pharmacologically active substance to the large intestine protects it from the acidic environment in the stomach. The pellet includes three components. The first component, a "bead", includes at least one pharmacologically active substance, microcrystalline cellulose, a pH-sensitive polymer, and optionally an osmotic agent. The second component is a "delayed release coating" and the third component is an "enteric coating".

DETAILED DESCRIPTION OF THE INVENTION

In accordance with the present invention, a pharmaceutical formulation, in the form of a pellet is provided for the controlled release delivery of pharmacologically active substances to the lower portion of the gastrointestinal tract, more specifically, the large intestine. The pellet formulation includes three components.

The first component, the core, is a "bead" which includes one or more pharmacologically active substances, microcrystalline cellulose, a pH-sensitive polymer and optionally an osmotic agent. Examples of suitable pharmacologically active substances are proteins, which are unstable in the lower pH range of the gastrointestinal tract (i.e., pH less than about 5); drugs which can cause stomach irritation, such as non-steroidal anti-inflammatory agents, for example, indomethacin or theophylline; or drugs which are weak bases or salts thereof, such as nefazodone. More than one pharmacologically active substance may be included in the formulation. Microcrystalline cellulose is commercially available as Avicel PH101 or Emocel. While not wishing to be bound by theory, it is believed that the microcrystalline cellulose acts as the matrix of the bead and additionally as a spheronizing aid. A suitable pH-sensitive polymer is one which will swell with intestinal juices at the higher pH levels (pH greater than about 5), such as in the lower portion of the small intestine (ileum) and the large intestine and therefore release a predominant amount (greater than 85%) of the drug in these regions and not in the upper portion of the gastrointestinal tract such as the stomach and the upper portions of the small intestine (duodenum and jejunum). Any polymer which will swell with intestinal juices in the higher pH regions to permit controlled release delivery of the pharmacologically active substance in these higher pH regions is suitable. Exemplary polymers are carbomers and the sodium salts of carbomers. Carbomers are acidic polymers which will be useful for those drugs that are more stable in an acidic environment, while the sodium salts of carbomers will be useful for those drugs that are more stable in a basic environment. Examples of commercially available carbomers are Carbopol 934P and Carbopol 974P. Optionally an osmotic agent such as polyethylene glycol may be utilized in the bead component.

The second component of the pharmaceutical formulation is a "delayed release coating". This component is between the first component and the third component. The delayed release coating includes a pharmaceutically acceptable material which protects the bead to prevent drug release from the bead while the pellet is traveling through the duodenum in the pH region of between about 5 to 6.5. The second component includes a non-water soluble polymer, a plasticizer, and an antiagglomerating agent. Examples of non-water soluble polymers which are suitable for use include copolymers synthesized from acrylic and methacrylic acid esters with low quaternary ammonium group content, such as the commercially available Eudragit RS30D or ethyl cellulose, which is commercially available as Aquacoat. Exemplary plasticizers include triacetin, acetyl tributyl citrate, triethyl citrate, dibutyl-sebacate, and acetylated monoglycerides. Exemplary antiagglomerating agent include talc, titanium dioxide, magnesium stearate, and silicon dioxide.

The third component of the pharmaceutical formulation is an "enteric coating". This component is the outer most component and is such that it protects the second component and the bead while the pellet is traveling through the stomach in the acidic pH region of between 1 to 3. The enteric coating includes an anionic polymer such as cellulose acetate phthalate or cellulose acetate trimellatate. An example of a commercially available anionic polymer is Eudragit L30d. Other optional ingredients that can be included in the enteric coating are plasticizers and antiagglomerating agents. Suitable plasticizers and antiagglomerating agents are listed above in the description of the second component.

The pellets pass through the stomach first. The transit time for the stomach is approximately two hours and the pH of this region is approximately 1 to 3. The enteric coating component, allows the second component and the bead to remain substantially intact and thus prevents the pharmacologically active substance from being released in this region.

The pellets will then pass through the small intestine, which consists of the duodenum, jejunum and ileum. The transit time through the small intestine is approximately three hours and the pH of these regions is approximately 6 to 6.5. In the duodenum, the enteric coating will start to dissolve, however, the delayed release coating prevents the pharmacologically active substance from being released in this region. As the pellets move through the jejunum, the gastric juices will start penetrating the delayed release coating and contact the core which will start to swell such that approximately 5% of the drug will be released in the jejunum. As the pellets move through the ileum, the gastric juices will continue to penetrate the core and cause it to swell even further causing an additional amount (approximately 10%) of the drug to be released in the ileum.

The pellets will then pass through the large intestine which consists of the caceum (~8.5 cm), ascending colon (~20 cm), transverse colon (~45 cm), descending colon (~30 cm) and sigmoid colon (~40 cm). The pH of the large intestine is approximately 6.4 to 7.0 with a total transit time of approximately 35 hours. In this region, the core will continue swelling due to the pH of this region, and as a function of time. As the swelling increases, more drug will be released. Approximately 85% of the drug will be released in the large intestine, resulting in an accumulative release of 100% of the drug.

The pharmaceutical formulation is such that greater than 80% of the pharmacologically active substance is released after 12 to 24 hours. Preferably greater than 80% of the drug is released after 10 to 12 hours.

The preferred ranges of ingredients as a percentage of the total are as follows:

| I. Beads | |
| --- | --- |
| Drug substance | 5% to 30% |
| Microcrystalline cellulose | 40% to 70% |
| pH-sensitive polymer | 5% to 15% |
| Osmotic agent | 0% to 10% |
| II. Delayed Release Coating | |
| Non-water soluble polymer | 2% to 6% |
| Plasticizer | 0.2% to 1% |
| Antiagglomerating agent | 0.5% to 2% |
| III. Enteric Coating | |
| Anionic polymer | 10% to 20% |
| Plasticizer | 0% to 2% |
| Antiagglomerating agent | 0% to 5% |

The preferred ingredients and ranges as a percentage of the total are as follows:

| I. Beads | |
| --- | --- |
| Drug substance | 5% to 10% |
| Microcrystalline cellulose | 45% to 65% |
| Carbomer | 7% to 11% |
| Osmotic agent | 0% to 8% |
| II. Delayed Release Coating | |
| Eudragit RS 30D | 2% to 4% |
| Triacetin | 0.5% to 0.75% |
| Talc | 0.5% to 1.75% |
| III. Enteric Coating | |
| Eudragit L30D | 13% to 17% |
| Triacetin | 1% to 2% |
| Talc | 2% to 3% |

The core ingredients are wet granulated, extruded, spheronized then dried and screened to select beads between about 10 to 40 mesh in size, as known in the art according to current good manufacturing practices. The beads are then coated, first with the delayed release coating mixture and then the enteric coating mixture as known in the art. It is preferred that the delayed release coating is about 10μ to about 20μ in thickness and the enteric coating is greater than about 10μ in thickness.

The following examples and preparations describe the manner and process of making and using the preferred embodiments of the invention and are illustrative rather than limiting. It should be understood that there may be other embodiments which fall within the spirit and scope of the invention as defined by the claims appended hereto.

EXAMPLE 1

The beads included theophylline as a model pharmacological agent, Avicel PH101 as the microcrystalline cellulose and Carbopol 934P as the pH-sensitive polymer. The beads were prepared by granulating the mixture with water in a planetary mixer, extruding through a NIKA extruder equipped with a 1.2 mm screen and spheronizing at 650 RPM for three minutes using a Caleva spheronizer. The beads were then dried in a fluid bed dryer to a moisture level of less than two percent and screened prior to coating to obtain a uniform size fraction. The beads were coated in a fluid bed coater equipped with a Wurster column.

The delayed release coating was prepared by first mixing water, talc and triacetin in an Ultra-Turrax homogenizer. To this mixture was added the polymer dispersion of Eudragit RS-30D. The resulting mixture was continuously stirred on a magnetic stir plate during the coating operation. A 1 to 1.5 kg charge of core beads was placed into a Glatt GPCG-1 fluid bed coater equipped with a Wurster column set at ½ inch. The delayed release coating mixture was then sprayed onto the beads at a rate of 9 grams per minute using a Master flex pump. A nozzle with a port size of 0.8 mm was used with an atomizing air pressure of 1.8 Bar to deliver the delayed release coating mixture to the beads. The product temperature was kept at 25° C. by adjusting the inlet air temperature to approximately 42° C. The lines to the Masterflex pump were rinsed with water before applying the enteric coating to the beads.

The enteric coating was prepared by first mixing water, talc and triacetin in an Ultra-Turrax homogenizer. To this mixture was added the polymer dispersion of Eudragit L30D. The enteric coating dispersion was then sprayed on to the beads (having the delayed release coating) at a rate of 10–11 grams per minute. The inlet air temperature was set at approximately 44° C. to obtain a product temperature of approximately 25° C. Finally the beads coated with the delayed release coating and the enteric coating were cured in the fluid bed coater for 1 hour at a product temperature of 40° C.

Dissolution testing was done with a Waters Automatic Dissolution/HPLC Interface System. The dissolution media was adjusted to a uniform ionic strength of 0.15 with sodium chloride. The ingredients are listed in Table 1.

TABLE 1

| Quantitative List of Ingredients | | |
| --- | --- | --- |
| | grams | % of total |
| I. Beads | | |
| Theophylline | 150 | 7.52 |
| Carbopol 934P | 210 | 10.53 |
| Avicel PH101 | 1140 | 57.15 |
| II. Delayed Release Coating | | |
| Eudragit RS30D (225 g @ 30% solids) | 67.5 | 3.38 |
| Triacetin | 13.5 | 0.68 |
| Talc | 33.75 | 1.69 |
| III. Enteric Coating | | |
| Eudragit L30D (1000 g @ 30% solids) | 300 | 15.04 |
| Triacetin | 30 | 1.50 |
| Talc | 50 | 2.51 |

EXAMPLE 2

Using the procedure of Example 1, a pellet, in accordance with the present invention, having the following ingredients was prepared:

| | grams | % of total |
| --- | --- | --- |
| I. Beads | | |
| Theophylline | 120 | 7.71 |
| Carbopol 934P | 168 | 10.80 |
| Avicel PH101 | 792 | 50.89 |
| Polyethylene glycol 400 | 120 | 7.71 |

-continued

|  | grams | % of total |
|---|---|---|
| II. Delayed Release Coating | | |
| Eudragit RS30D (120 g @ 30% solids) | 36 | 2.31 |
| Triacetin | 7.2 | 0.46 |
| Talc | 9.0 | 0.58 |
| III. Enteric Coating | | |
| Eudragit L30D ((800 g @ 30% solids) | 240 | 15.42 |
| Triacetin | 24 | 1.54 |
| Talc | 40 | 2.57 |

EXAMPLE 3

Using the procedure of Example 1, a pellet, in accordance with the present invention, having the following ingredients was prepared:

|  | grams | % of total |
|---|---|---|
| I. Beads | | |
| Theophylline | 120 | 7.54 |
| Carbopol 934P | 168 | 10.56 |
| Avicel PH101 | 792 | 49.78 |
| Polyethylene glycol 3350 | 120 | 7.54 |
| II. Delayed Release Coating | | |
| Eudragit RS30D (200 g @ 30% solids) | 60 | 3.77 |
| Triacetin | 12 | 0.75 |
| Talc | 15 | 0.94 |
| III. Enteric Coating | | |
| Eudragit L30D (800 g @ 30% solids) | 240 | 15.08 |
| Triacetin | 24 | 1.51 |
| Talc | 40 | 2.51 |

EXAMPLE 4

Using the procedure of Example 1, a pellet, in accordance with the present invention, having the following ingredients was prepared with a mixture of alcohol and water 70/30 replacing water as the granulating solution:

|  | grams | % of total |
|---|---|---|
| I. Beads | | |
| Theophylline | 120 | 7.67 |
| Sodium salt of Carbopol 934P | 120 | 7.67 |
| Avicel PH101 | 960 | 61.35 |
| II. Delayed Release Coating | | |
| Eudragit RS30D (140 g @ 30% solids) | 42 | 2.68 |
| Triacetin | 84 | 0.54 |
| Talc | 105 | 0.67 |
| III. Enteric Coating | | |
| Eudragit L30D (800 g @ 30% solids) | 240 | 15.34 |
| Triacetin | 24 | 1.53 |
| Talc | 40 | 2.56 |

What is claimed is:

1. A three component pharmaceutical formulation comprising: a first component which includes at least one pharmacologically active substance, microcrystalline cellulose, a pH-sensitive polymer which is a carbomer or a sodium salt of a carbomer, and optionally an osmotic agent; a second component which is a delayed release coating wherein said delayed release coating includes a non-water soluble polymer, a plasticizer and an antiagglomerating agent; and a third component which is an enteric coating.

2. The formulation as recited in claim 1 wherein greater than 80% of the pharmacologically active substance is released in the large intestine.

3. The formulation as recited in claim 1 wherein the enteric coating includes an anionic polymer and optionally a plasticizer.

4. The formulation as recited in claim 3 wherein the anionic polymer is cellulose acetate phthalate or cellulose acetate trimellatate.

5. The formulation as recited in claim 3 wherein the enteric coating optionally includes an antiagglomerating agent.

6. The formulation as recited in claim 1 wherein the pharmacologically active substance is a protein.

7. The formulation as recited in claim 1 wherein the pharmacologically active substance is a non-steroidal anti-inflammatory agent.

8. The formulation as recited in claim 3 wherein the plasticizer is triacetin, acetyl tributyl citrate, triethyl citrate, dibutyl-sebacate or acetylated monoglycerides.

9. The formulation as recited in claim 1 wherein the osmotic agent is present.

10. The formulation as recited in claim 9 wherein the osmotic agent is polyethylene glycol.

11. The formulation as recited in claim 1 wherein the non-water soluble polymer is a copolymer synthesized from acrylic or methacrylic acid ester having a low quaternary ammonium group content or ethyl cellulose.

12. The formulation as recited in claim 5 wherein the antiagglomerating agent is talc, titanium dioxide, magnesium stearate or silicon dioxide.

13. The formulation as recited in claim 1 wherein the plasticizer is triacetin, acetyl tributyl citrate, triethyl citrate, dibutyl-sebacate or acetylated monoglycerides.

14. The formulation as recited in claim 1 wherein the antiagglomerating agent is talc, titanium dioxide, magnesium stearate or silicon dioxide.

15. The formulation of claim 1 wherein: the first component comprises between about 5% to 30% of the pharmacologically active substance, between about 40% to 70% of microcrystalline cellulose, between about 5% to 15% of pH-sensitive polymer and between about 0% to 10% of osmotic agent; the second component comprises between about 2% to 6% of non-water soluble polymer, about 0.2% to 1% of plasticizer and between about 0.5% to 2% of antiagglomerating agent; and the third component comprises between about 10% to 20% anionic polymer, 0% to 2% of plasticizer and 0% to 5% of antiagglomerating agent.

* * * * *